United States Patent [19]

Huntzinger

[11] Patent Number: 5,166,531
[45] Date of Patent: Nov. 24, 1992

[54] LEAF-END CONFIGURATION FOR MULTILEAF COLLIMATOR

[75] Inventor: Calvin J. Huntzinger, San Carlos, Calif.

[73] Assignee: Varian Associates, Inc., Palo Alto, Calif.

[21] Appl. No.: 740,164

[22] Filed: Aug. 5, 1991

[51] Int. Cl.⁵ .............................. G21K 1/02
[52] U.S. Cl. ................... 250/505.1; 378/152; 378/150
[58] Field of Search ............ 250/505.1; 378/152, 378/151, 150, 147

[56] References Cited

U.S. PATENT DOCUMENTS

| | | | |
|---|---|---|---|
| 3,227,880 | 1/1966 | Wideroe | 250/505.1 |
| 4,157,475 | 6/1979 | Stock et al. | 250/505.1 |
| 4,534,052 | 8/1985 | Milcamps | 378/152 |
| 4,672,212 | 6/1987 | Brahme | 250/505.1 |
| 4,868,843 | 9/1989 | Nunan | 378/152 |
| 5,012,506 | 4/1991 | Span et al. | 378/152 |

OTHER PUBLICATIONS

Sutherland, W. H. et al., "Design Principles of Telecobalt Collimators", Physics in Medicine and Biology, 22, 1189-1196 (1977).

Maleki, N. et al., "Analysis of the Field Defining Properties of a Multi-Leaf Collimator", Medical Physics, vol. 10, No. 4, (abstract), Jul./Aug. 1983.

Primary Examiner—Jack I. Berman
Attorney, Agent, or Firm—Sheri M. Novack

[57] ABSTRACT

A multileaf collimator for use in therapeutic radiology treatment systems for producing irregular shaped radiation fields in order to shield normal tissue or critical organs. A multileaf collimator following the present invention includes leaves designed such that the collimator exhibits penumbra which is minimized and generally uniform for positions that are equidistant from the central axis of the radiation field. The shape of each leaf end includes an asymmetric central portion and a flat portion on either side of the central portion. The central portion is designed such that geometric penumbra and transmission penumbra are equalized. The flat portions on either side of the central portion are coincident with a tangent drawn from the edge of the radiation source to a reference plane when the leaf is in the fully retracted or fully extended positions.

30 Claims, 7 Drawing Sheets

LEAF-END CONFIGURATION FOR MULTILEAF COLLIMATOR

BACKGROUND OF THE INVENTION

This invention relates to a multileaf collimator for use in a radiation system used to shape and control spatial distribution of the radiation field intensity.

Conventional radiation treatment of a tumor in a patient is carried out by planning the radiation beam angles and dosage, taking into consideration safety factors with respect to the patient's normal tissue and organs located in the path of the proposed radiation beam. The usual treatment field shapes result in a three-dimensional treatment volume which includes segments of normal tissue and organs (a safety margin around the tumor), thereby limiting the dose that can be given to the tumor. Cure rates for many tumors are a sensitive function of the dose they receive. The dose that can be delivered to the tumor can be increased if the portion of the normal tissue or organs receiving dose can be reduced. Techniques are under development to make the treatment volume conform more closely to the shape of the tumor volume. This permits higher dose to tumors and less damage to normal tissue and organs, with its attendant positive effects on the health of the patient. The techniques typically involve moving the jaw-blocks during treatment, scanning the radiation beam over the volume to be treated or using a multileaf collimator. Multileaf collimators can provide a similar function as the conventional jaw-blocks. In addition, each individual segment or leaf in a multileaf collimator is usually independently positionable. The radiation beam is directed at the ends and sides of the collimator leaves such that the beam is limited to the desired treatment area to be irradiated, while shielding the normal tissue and organs.

Radiation beam penumbra occurs in systems equipped with multileaf collimators at the edges of the radiation field where the radiation intensity decreases with distance from the full intensity region of field. This phenomenon is a combination of geometric penumbra due to the radiation source size and transmission penumbra due to penetration of the radiation beam through the ends of the multileaf collimator leaves. Geometric penumbra is a function of the source size, the thickness of the leaves, the distance of the leaves from the source and the distance of the reference plane from the source. Transmission penumbra is a function of material the leaves are made from, the thickness of the leaves and the energy of the radiation beam.

In the technical paper, "Design Principles of Telecobalt Collimators", W. H. Sutherland and C. W. Smith, Physics in Medicine and Biology, 22, 1189–1196 (1977), the authors clearly show that minimum geometric penumbra is produced when radiation collimators are pointed at the side of the radiation source.

The penumbra produced by square-end or simple curved-end linear-motion multileaf collimators at points equidistant from the central axis of the radiation beam is not equal. This can be explained as an effect of geometric penumbra. When the leaf is fully retracted from the central axis, the radiation field is defined by the portion of the leaf end furthest from the radiation source, the distal portion. In the fully extended position, the portion of the leaf end closest to the radiation source defines the radiation field, the proximal portion. The proximal portion of the extended leaf end produces greater geometric penumbra than the distal portion of the retracted leaf for positions equidistant from the central axis of the radiation field because the radiation source is perceived as larger from the proximal portion.

Typically, megavoltage radiation beams are very penetrating. Collimators and jaw-blocks that are used to sharply define the shape of radiation beam are typically made from high density, high atomic number materials and are usually several inches thick. If thinner sections, with less attenuation, are used then the edge of the radiation field is not defined as sharply, hence the transmission penumbra is larger.

U.S. Pat. No. 4,672,212 to Brahme discloses a multileaf collimator in which the entire leaf body is curved. The curved leaf follows a curved path of travel such that the flat leaf end is always tangent to the radius of an imaginary circle having its center at the radiation source. This configuration minimizes transmission penumbra. However, the curved leaf body results in complicated leaf mounting structures which are mechanically complex, physically large, difficult to retrofit onto existing systems and expensive to manufacture.

Linear motion multileaf collimators or jaw-blocks are easier to fabricate and assemble but their use typically produces larger penumbra. Leaf ends having simple curves of large radius produce acceptable penumbra for small field sizes. However, the transmission penumbra becomes progressively worse for larger fields. Leaf ends having small radii produce large penumbra for all field sizes. Also, penumbra for leaf ends at equidistant positions about the central axis are not equal.

The technical paper, "Analysis of the Field-Defining Properties of a Multileaf Collimator", N. Maleki and P. Kijewski, Medical Physics, 10, 518 (abstract) (1983), contains a figure which shows calculated penumbra for a range of simple, curved leaf-ends with a constant radius. A figure from the paper is reproduced here as FIG. 6. As discussed above, leaf ends having curves of large radius produce acceptable penumbra for small field sizes. However, the penumbra becomes progressively worse for larger fields. Leaf ends having curves of small radius produce large penumbra for all field sizes.

U.S. Pat. No. 4,868,843 to Nunan issued on Sep. 19, 1989, assigned to the assignee of the present invention, is hereby incorporated by reference thereto. Nunan discloses a multileaf collimator assembly which can be retrofitted as an accessory to existing systems. Alternatively, the Nunan multileaf collimator may be incorporated into the design of a new radiation system. The multiple leaves are independently positionable and travel in a straight line along the longitudinal axis of the individual leaves. This patent incorporates leaves with simple curved ends.

U.S. Pat. No. 4,534,052 to Milcamps describes a linear-motion jaw-block having a curved end. The jaw-block is movable only in a retractable direction with respect to the central axis of the radiation beam. The curved jaw-block end is defined by a simple arc of large radius having a center of curvature positioned on the proximal jaw-block surface, closest to the radiation source. The radiation beam of Milcamps is defined by a sharp edge at the intersection of the "active surface" and the distal surface when the jaw-block is at the furthest retracted position from the central axis of the radiation beam. This sharp edge readily transmits the penetrating radiation beam causing excessive transmission penumbra. Additionally, the asymmetric jaw-block "active surface" produces unacceptable penumbra if extended beyond the central axis of the radiation beam, by transmission of penetrating radiation through the sharp edge, at the intersection of the proximal surface, closest to the radiation source, and the "active surface".

SUMMARY OF THE INVENTION

The present invention relates to a multileaf collimator for use in a radiation system which provides uniform, minimized penumbra over the full range of travel of the collimator leaves, including travel across central axis of the radiation beam. In radiation therapy systems equipped with multileaf collimators, the multileaf collimator is contained within or attached to the radiation head. Irregular field shapes, conforming to the prescribed treatment volume, are established by moving the leaves to the desired positions.

The present invention is preferably used in conjunction with a plurality of elongated collimator leaves arranged in a side-by-side array. Two such arrays are positioned with the leading ends of each array facing the other in opposed relationship on opposite sides of the central axis of the radiation beam.

It is an object of the present invention to equalize geometric penumbra and transmission penumbra over the full range of leaf end travel by optimizing the amount of material used to define the edge of the radiation beam. The proximal portion of the leaf-end, with greater geometric penumbra, is preferably given more material to define the radiation field. This greater attenuation more sharply defines the edge of the field, hence produces smaller transmission penumbra values. Conversely, material is also preferably taken away from the distal portion of the leaf-end, which has smaller geometric penumbra, causing it to produce less sharply defined radiation field edges, hence greater transmission penumbra.

The penumbra produced by the distal and proximal portions of the leaf end will, therefore, be similar for points equidistant from the central axis of the radiation beam. This equalization of geometric and transmission penumbra is achieved by distally offsetting the axis of symmetry of each respective collimator leaf end with respect to the longitudinal axis of the leaf. Thus, it will not be necessary for the treatment planner of the radiation system to differentiate between retraction or extension of the collimator leaves.

In addition, it is an object of the present invention to minimize penumbra. This is accomplished by pointing the proximal and distal tangential leaf end surfaces at the edge of the radiation source. The minimized penumbra will allow the treatment field to more closely conform to the tumor volume.

Other features and advantages of the present invention will appear from the following descriptions in which the preferred embodiment has been set forth in detail in conjunction with the accompanying drawings.

DETAILED DESCRIPTION OF THE PREFERRED EMBODIMENT

Figure 1:
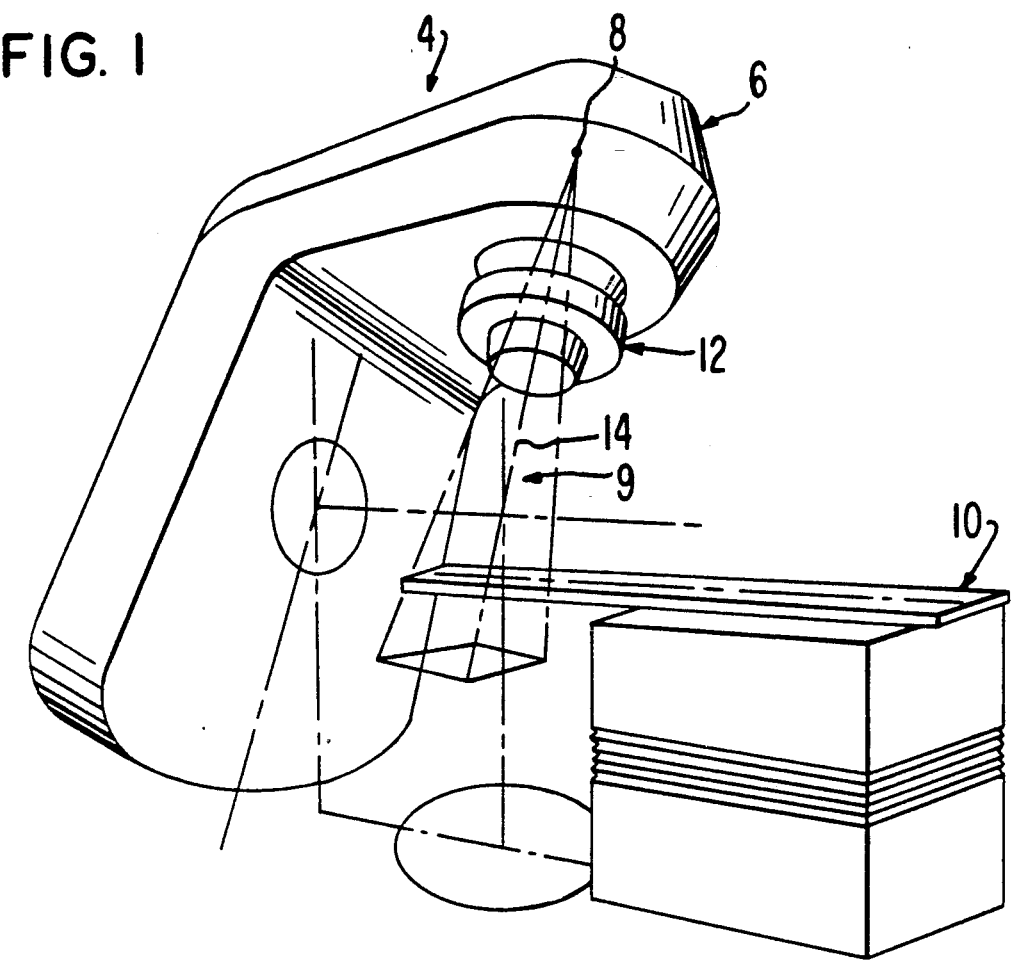
FIG. 1 is a perspective view of a radiation therapy system.
Figure 3:
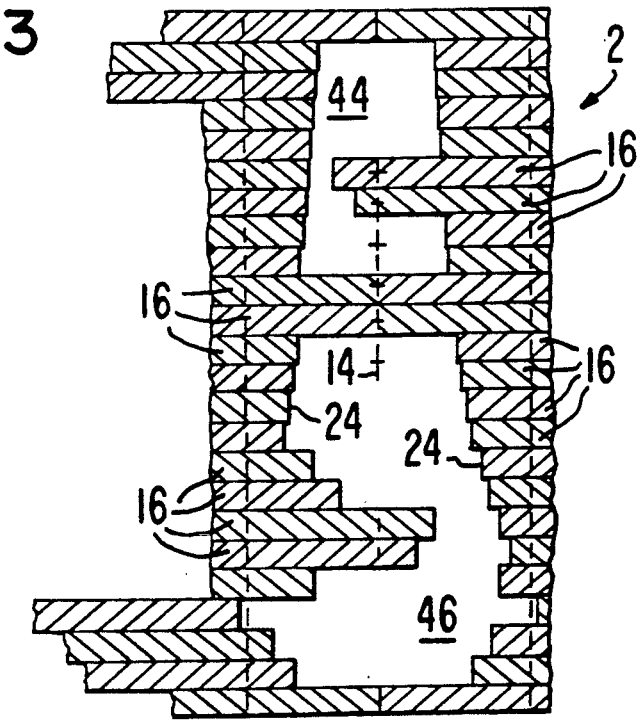
FIG. 3 is a top plan view of a multileaf collimator as seen from the source of the radiation therapy system.
Figure 2:
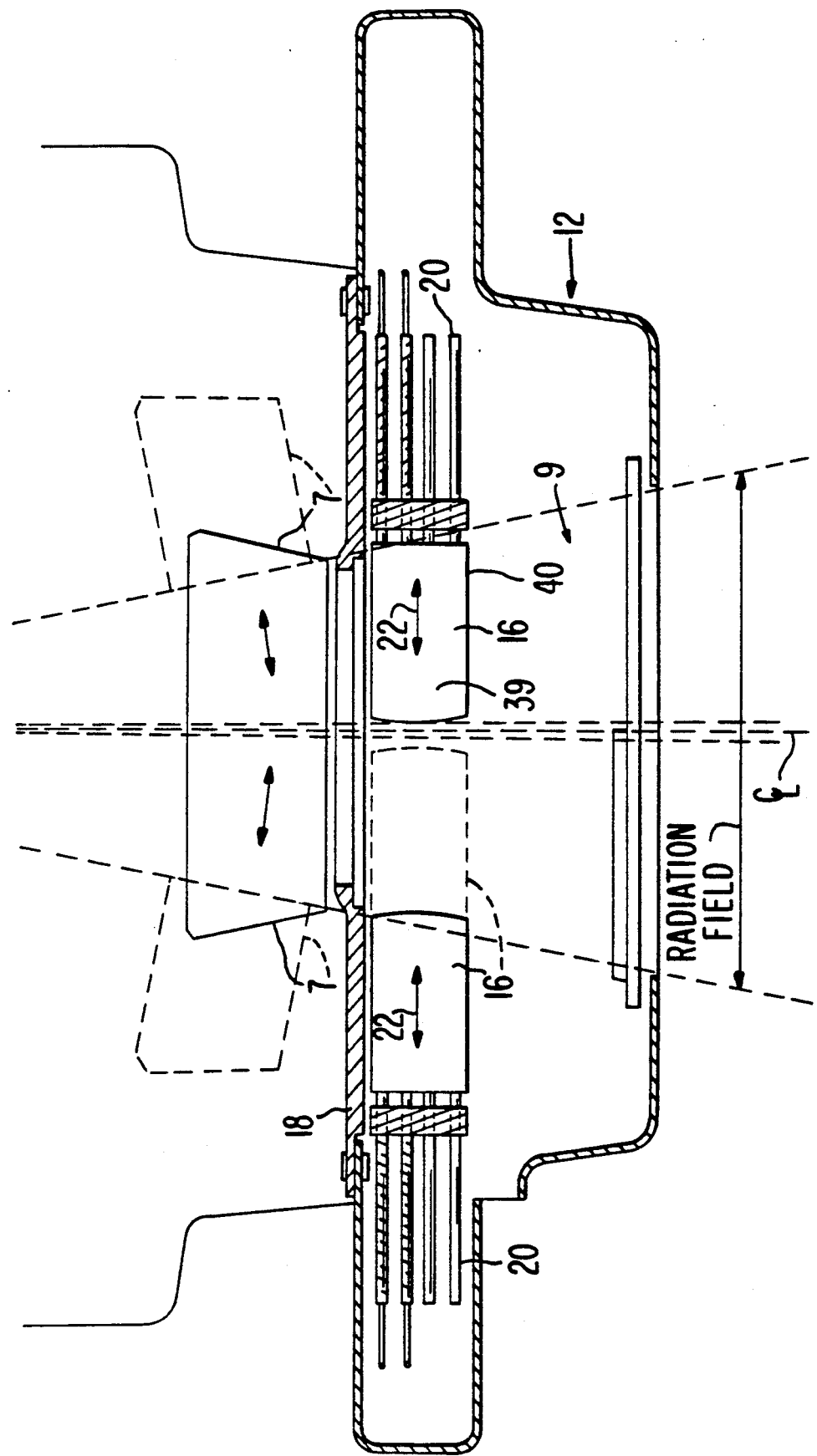
FIG. 2 is a side sectional view of the collimator of the present invention positioned within the radiation therapy system.

Referring now to FIGS. 1 to 5, a multileaf collimator 2 is illustrated in accordance with the present invention. A gantry 4 is shown in FIG. 1. Gantry 4 includes a radiation head 6 for housing a radiation source 8. A patient support assembly 10 is positioned within a radiation beam 9. Multileaf collimator 2 is housed within a multileaf collimator system 12. A central axis 14 of radiation beam 9 is coincident with the central axis of multileaf collimator 2. A pair of conventional movable collimators, identified as jaw-blocks or jaws 7 is positioned to generally align the radiation beam with the treatment field to be irradiated, as seen in FIG. 2. The radiation treatment volume is dependent on the shape of the tumor, as seen from radiation source 8. It is desirable to generate a shaped treatment field to conform exactly to the shape of the tumor so as to permit a greater dose of radiation to be delivered to the tumor. Therefore a plurality of leaves 16 are independently movable with respect to jaws 7 in a longitudinal direction 22, oriented generally perpendicular to central axis 14.

Figure 4:
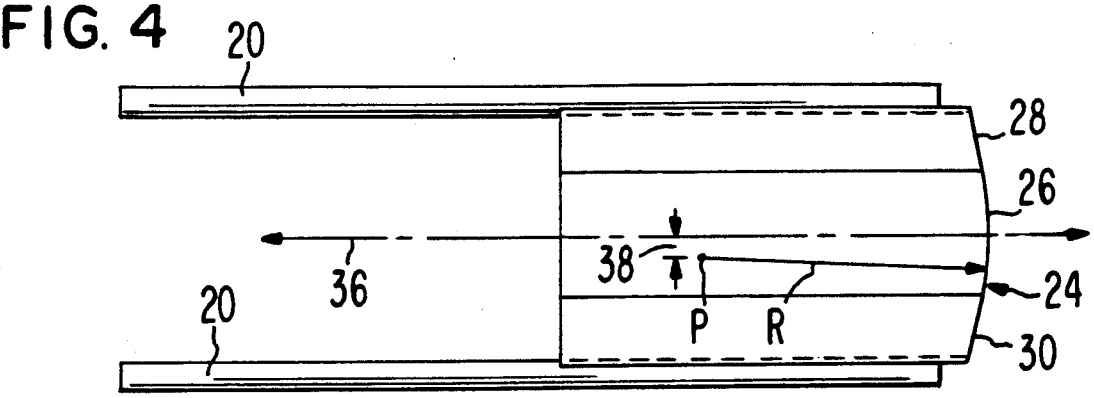
FIG. 4 is a side sectional view of a single leaf of the multileaf collimator.
Figure 5:
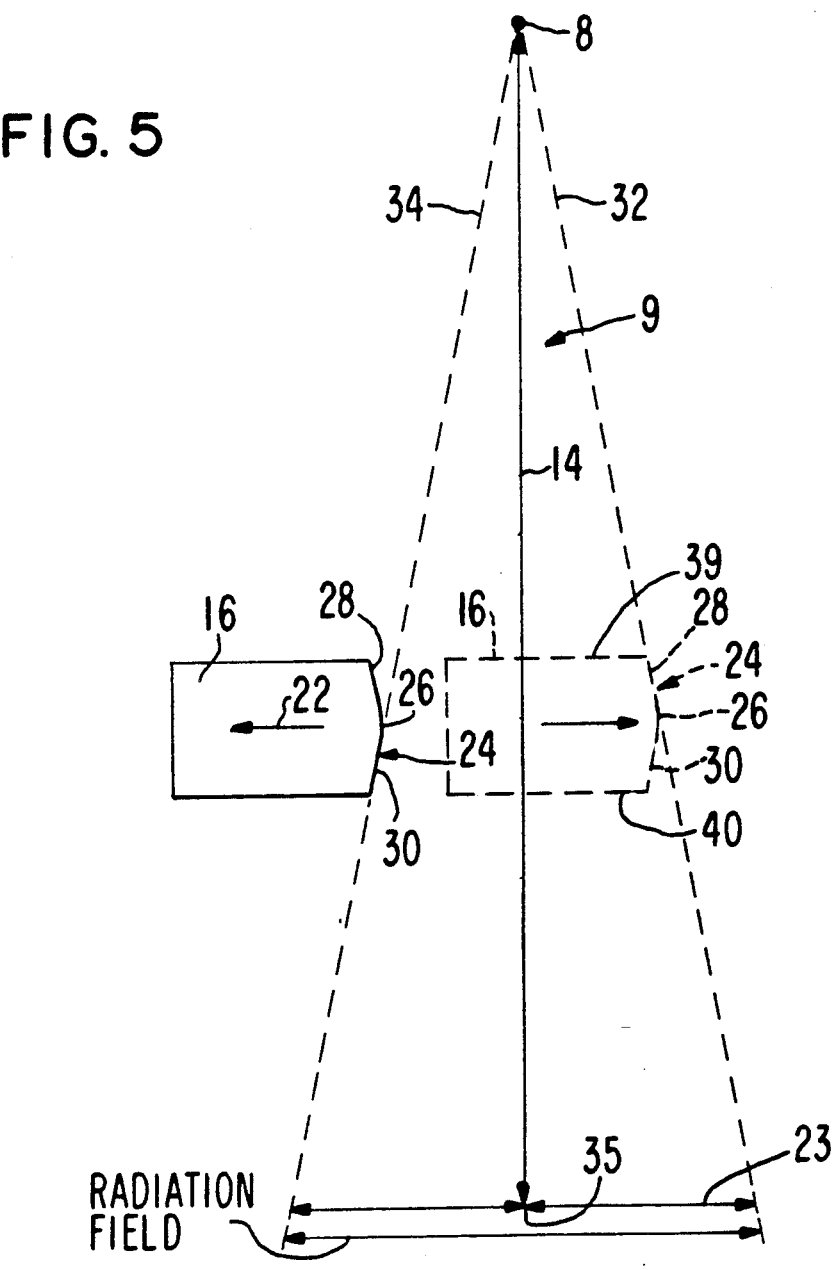
FIG. 5 is a schematic view illustrating a leaf in its fully withdrawn position, thereby defining the tangent. The leaf is shown in its fully extended position in phantom.
Figure 6:
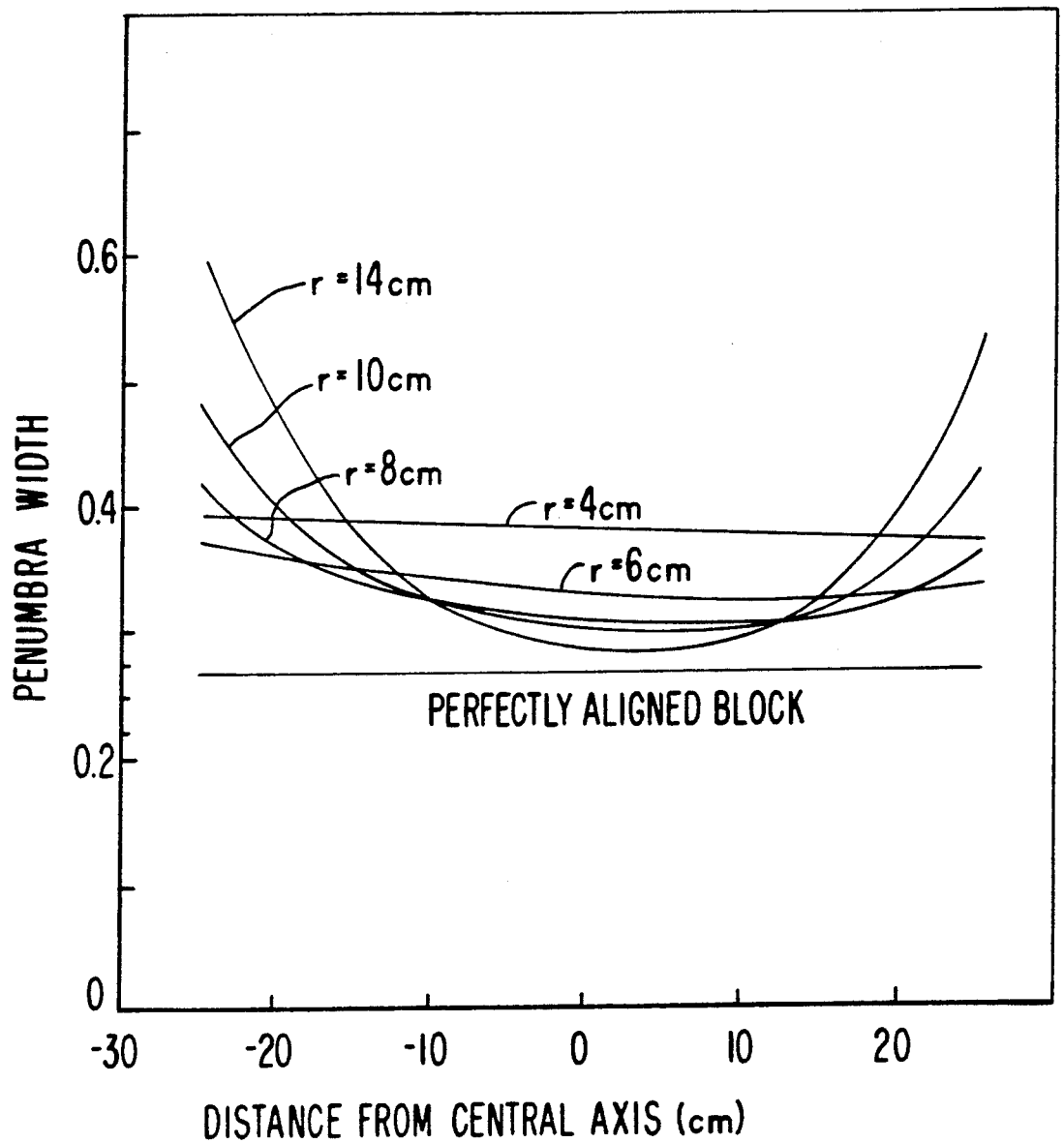
FIG. 6 illustrates calculated penumbra for a range of simple, curved leaf ends of constant radius.

Referring to FIGS. 4 and 5, each leaf 16 includes a leaf end 24 generally transverse to longitudinal direction 22. The particular shape of the leaf ends ultimately determines the size of penumbra generated in conjunction with a radiation field. Furthermore, the shape of leaf end 24 determines the extent to which leaves 16 can be extended across central axis 14, while still producing a radiation field with acceptable penumbra. Leaves 16 are movable in longitudinal direction 22 from a fully retracted position as seen in solid lines in FIG. 5 to a fully extended position as seen in dashed lines in FIG. 5. In the preferred embodiment, the distance from central axis 14 to each of the fully withdrawn and fully extended positions is 20 cm, at a reference plane 23 positioned 100 cm from the source of radiation. Therefore, coverage may occur over the entire 40 cm range of motion, as measured at reference plane 23. This range of motion allows other conformal therapy methods to be employed with multileaf collimators employing leaf ends in accordance with the present invention. Isocenter 35 is positioned on reference plane 23 at its intersection with central axis 14.

The difference in geometry between a proximal surface 39 of leaf 16 and a distal surface 40 of the leaf causes proximal surface 39 to produce penumbra values that are greater than distal surface 40 because radiation source 8 appears larger, as seen from the proximal position. The geometric penumbra is dependent on the size of radiation source 8, the distance from the radiation source to either distal surface 40 or proximal surface 39, and the distance from radiation source 8 to reference plane 23. The equation for geometric penumbra, by considering similar traingles, is:

penumbra=(source size)[(reference plane
distance)-(leaf surface distance)]/(leaf surface
distance)

In the preferred embodiment, proximal surface 39 is 48.2 cm from the radiation source 8 while distal surface 40 is 53.4 cm from the radiation source. From the above equation, the geometric penumbra factor for the distal surface 40 will be: (source size) (0.873) while the geometric penumbra factor for proximal surface 39 will be (source size) (1.075). Therefore, in the preferred embodiment, the geometric penumbra for distal surface 40 will be (0.873/1.075) or 0.812 times as large as the geometric penumbra for proximal surface 39.

The geometric penumbra factors calculated above must be compensated with transmission penumbra. Referring to FIG. 4, this is done by offsetting the axis of symmetry of the leaf end distally from the longitudinal axis 36 of leaf 16 by an offset distance 38. The amount of offset 38 is chosen such that the amount of radiation attenuation in offset 38 is equal to the geometric penumbra factor between proximal and distal surfaces 39, 40. For the preferred embodiment, the offset thickness is calculated as follows:

$$e^{-ux}=0.812,$$

where 0.812 is the geometric factor calculated above
u is the linear attenuation coefficient
x is the desired offset distance to solve for Table 1 lists calculated linear attenuation coefficients of several materials for common megavoltage x-ray beams. The calculated narrow-beam linear attenuation coefficients listed in Table 1 can be used for megavoltage x-ray beams to calculate the required material thickness to achieve the desired offset.

TABLE 1

Calculated Narrow-Beam, Linear Attenuation Coefficients.
$(inch^{-1})$

|    | Atomic Number | Density $(g/cm^3)$ | 4 MV | 6 MV | 10 MV | 15 MV | 25 MV |
|----|---|-------|-------|-------|-------|-------|-------|
| Al | 4  | 2.70  | 0.365 | 0.316 | 0.256 | 0.215 | 0.186 |
| V  | 23 | 6.11  | 0.782 | 0.687 | 0.581 | 0.505 | 0.462 |
| Fe | 26 | 7.87  | 1.06  | 0.924 | 0.812 | 0.708 | 0.667 |
| Cu* | 29 | 8.96 | 1.21  | 1.05  | 0.924 | 0.806 | 0.759 |
| Sn | 50 | 7.30  | 0.958 | 0.869 | 0.802 | 0.745 | 0.735 |
| W  | 74 | 17.0  | 2.53  | 2.27  | 2.15  | 1.97  | 1.98  |
| Pb* | 82 | 11.3 | 1.60  | 1.51  | 1.43  | 1.31  | 1.32  |

*Copper data scaled from iron data and lead data scaled from tungsten data, accounting for differences in density.

For leaves constructed of tungsten, the linear attenuation coefficient can be taken as 2.0 $inches^{-1}$. Substitution of the linear attenuation coefficient into the above equation yields an offset of 0.104 inches. Thus, in the preferred embodiment having leaves 16 constructed of tungsten, the axis of symmetry of the leaf ends 24 should have an offset 38 on the distal side of longitudinal axis 36 of leaves 16 of 0.104 inches.

A first flat end 28 and a second flat end 30 are directed at the edge of the radiation source when leaf 16 is fully extended or fully retracted, respectively, as seen in FIG. 5. A central portion 26 of leaf end 24 is an arc of fixed radius, as measured from the point P. The radius of central portion 26 influences the overall penumbral performance of the leaf end. In the preferred embodiment, the radius of curvature R is 8 cm.

In operation, jaw-blocks 7 are positioned relative to patient support assembly 10 at the generally desired location such that the radiation field is positioned in the approximate desired area for treatment. Leaves 16 are then driven on rails 20 to locate each respective leaf in the desired position for exactly defining the treatment volume of the tumor. First and second flat ends 28, 30 and central portion of leaf end 24 allow leaves 16 to be positioned on either side of central axis 14, as seen in FIG. 5, while maintaining equal penumbra values for positions equidistant from central axis 14.

Figure 7:
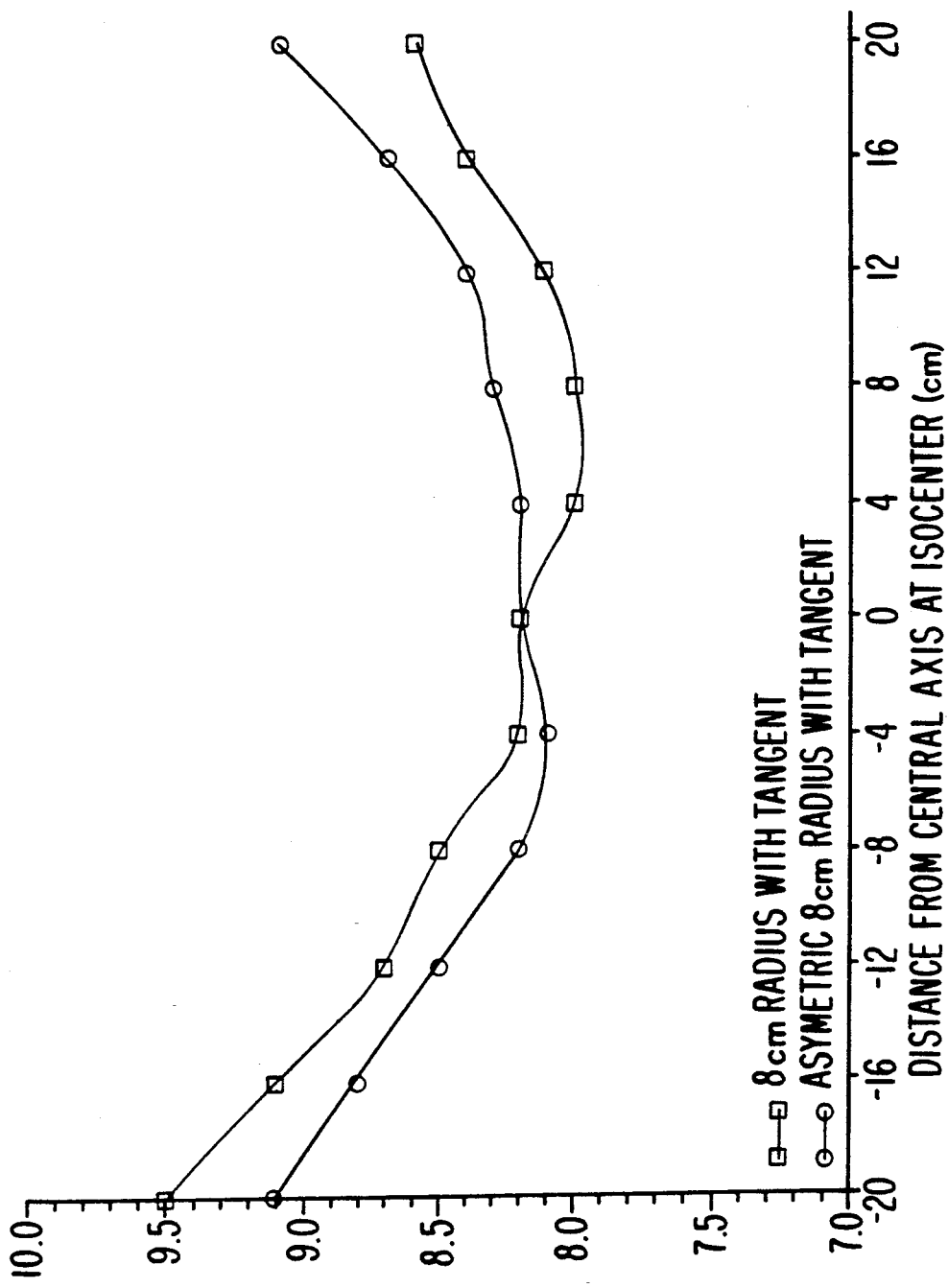
FIG. 7 illustrates penumbra calculated for the present invention over its range of operation.

The calculated multileaf penumbra is shown in FIG. 7. The figure represents leaf ends 16 retracted away from central axis 14 as positive position values, while leaf positions extended beyond central axis 14 are represented by negative position values.

FIG. 7 shows the calculated penumbra for a simple 8 cm constant radius, and an asymmetric 8 cm radius with flat surface tangents. (The asymmetric configuration can be seen in FIG. 4.) In both cases, the calculated penumbra values show the largest differences at the largest displacements from central axis, as is expected.

From these positions at long displacements from central axis, the difference between the penumbra values smoothly diminish. At central axis, there is no difference between the simple 8 cm radius and the asymmetric 8 cm radius with tangents.

Although the penumbra generated by distal portion 40 of leaf 16 has been increased at large retractions from central axis, the penumbra for leaf positions near central axis has not increased.

The asymmetric leaf end shape of the present invention has an additional benefit. Second flat end 30 is shorter when leaf end 24 has an asymmetric configuration than if the leaf end 24 were symmetric about longitudinal axis 36 of leaf 16. As leaf 16 is retracted away from central axis 14, second flat end 30 defines the edge of the radiation field. It also rescatters charged secondary particles back into radiation beam 9. These charged secondary particles (typically electrons and positrons) increase the surface dose in the reference plane 23 and cause the depth of the maximum dose in the reference plane to vary as a function of the size of radiation beam 9. It is desirable to minimize both of these effects, and providing a shorter leaf second flat end 30 accomplishes this. The shorter surface makes it less probable for charged secondary particles to be rescattered into the radiation beam 9.

ALTERNATE EMBODIMENTS

Figure 8:
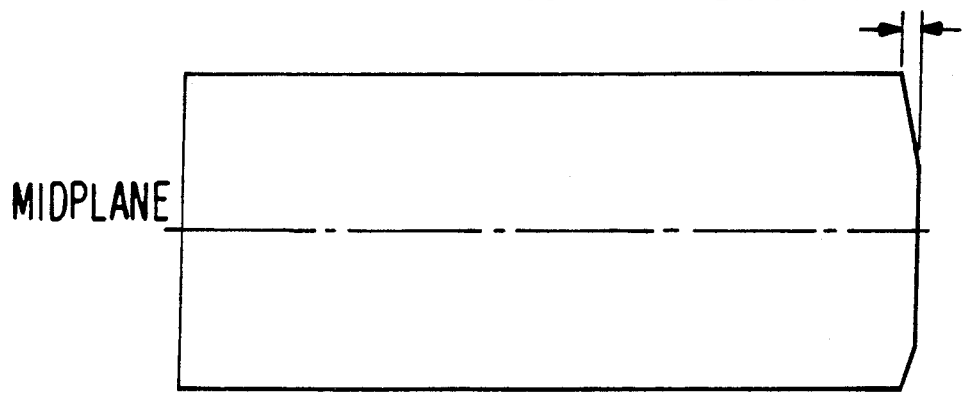
FIGS. 8-11 illustrate alternate embodiments of an asymmetric radius leaf end.

FIG. 8 shows an alternate embodiment of the asymmetric leaf end where the asymmetric end is approximated by a polygon. Clearly, the limit of a multifaceted polygon is a curved surface. The advantage of using a polygon is increased manufacturability, at the expense of increased transmission penumbra at the positions where the field edge is defined by a corner of the polygon.

Figure 9:
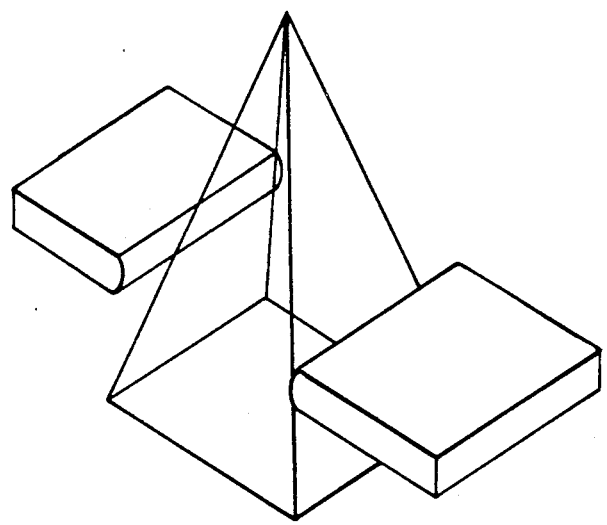

FIG. 9 shows an alternate embodiment of the asymmetric radius leaf end where the leaf extends in the full lateral extent of the radiation field, what is normally called a jaw-block.

Figure 10:
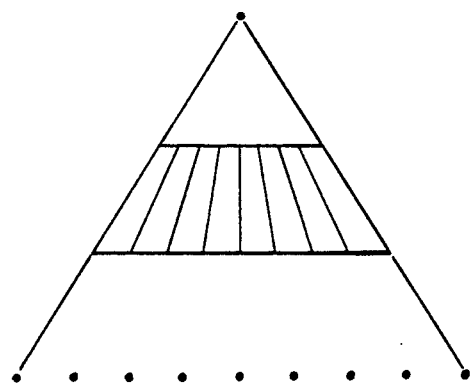

FIG. 10 shows an alternate embodiment of the asymmetric radius leaf end in which leaves 16 vary, dependent upon position. In the preferred embodiment, leaves 16 are identical for ease of fabrication. FIG. 10 shows leaves 16 with variable width in the direction parallel with rays from source 8. The embodiment of FIG. 10 would be required for multileaf collimators positioned close to an extended source, such that each leaf projected the same width onto the reference plane.

Figure 11:
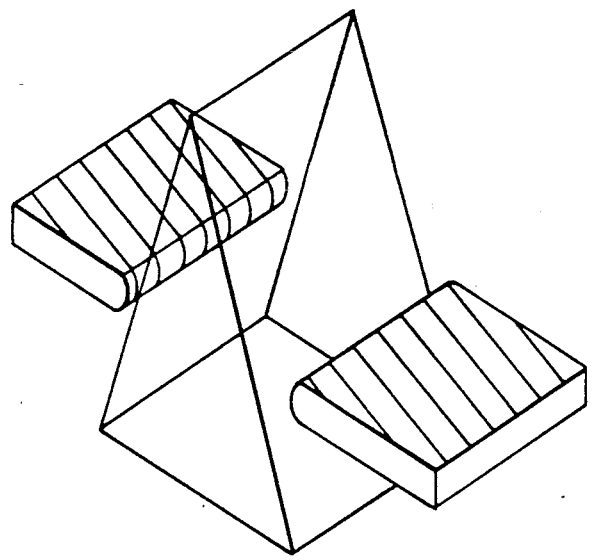

FIG. 11 shows an alternate embodiment of the asymmetric radius leaf end in which a linear radiation source is oriented perpendicularly to the motion of collimator leaves 16, rather than the generally circular sources typically used.

As discussed above, the first and second flat ends and the asymmetric leaf end of the present invention provides uniform and minimized penumbra over the full range of travel of the collimator leaves, including travel across the central axis of the radiation source. Furthermore, the equal penumbra values for points equidistant from the central axis simplifies operation of multileaf collimator requiring no differentiation between retraction and extension of the individual leaves. However, variations and modifications can be made to the preferred embodiment without departing from the scope of the present invention, which is limited only by the following claims.

I claim:

1. A multileaf collimator for use in a radiation system including a radiation source, said collimator having a plurality of elongated leaves, each leaf being movable in a longitudinal direction, and each terminating in a leaf end extending in a direction generally transverse to said longitudinal direction, said leaf end defining a central portion having one of a curved and polygonal configuration and a generally flat end portion.

2. The multileaf collimator of claim 1 wherein said leaf end includes an axis of symmetry offset distal from the longitudinal leaf axis with respect to the radiation source.

3. The multileaf collimator of claim 1 wherein said generally flat end portion comprises a flat end portion disposed on each radial end of said central portion.

4. The multileaf collimator of claim 1 wherein the radiation system includes a radiation source having a central axis for producing a therapeutic radiation field and wherein each said leaf is movable transversely with respect to said central axis of said radiation source from a fully retracted position to a fully extended position beyond said central axis in order to control the size and shape of said field in accordance with the positions of said leaves.

5. The multileaf collimator of claim 4 wherein said flat end portion comprises a first flat end portion coinciding with a tangent extending from the edge of said radiation source to said leaf end when said leaf end is disposed at said fully retracted position, and a second flat end portion coinciding with a tangent extending from the edge of said radiation source to said leaf end when said leaf end is disposed at said fully extended position.

6. The multileaf collimator of claim 5 wherein said central and flat portions of said leaf end extend in a direction generally parallel to said central axis.

7. The multileaf collimator of claim 6 wherein said first flat end portion is disposed proximate said radiation source and wherein said second flat end portion is disposed distal from said radiation source.

8. The multileaf collimator of claim 1 wherein said central portion comprises a curve of simple radius.

9. The multileaf collimator of claim 8 wherein said simple radius is symmetric about a point offset distal from the longitudinal axis of each leaf.

10. A multileaf collimator for use in a radiation system having a radiation source, said collimator having a plurality of elongated leaves, each leaf being movable in a longitudinal direction and terminating in a leaf end extending in a direction generally transverse to said longitudinal direction, each leaf end being symmetric about a point offset distally from the radiation source with respect to a centerline of the respective elongated leaf.

11. The collimator as defined in claim 10 wherein said point is located on the respective leaf.

12. The collimator as defined in claim 10 wherein each leaf is movable between a fully retracted mode and a fully extended mode, each leaf end comprising a central portion and a first flat zone formed in the proximal region of said leaf end, said first flat zone coinciding with a first tangent line extending from the edge of the source to said leading leaf end with the corresponding leaf in the fully extended mode.

13. The collimator as defined in claim 12 further comprising a second flat zone formed in the distal region of said leaf end, said second flat zone coinciding with a second tangent line extending from the edge of the source to said leading leaf end with the corresponding leaf in the fully retracted mode.

14. The collimator as defined in claim 13 wherein said central portion comprises a curved configuration.

15. The collimator as defined in claim 13 wherein said central portion comprises a polygonal configuration.

16. A multi-leaf collimator for use with a ray source defining a source axis, said collimator comprising a plurality of longitudinally elongated leaves arranged in a side-by-side array, each leaf terminating in a leading leaf end, each leaf being movable transversely with respect to a central axis generally parallel to said source axis, between a fully retracted mode and a fully extended mode, each leading end defining first and second generally flat zones separated by an intermediate zone generally continuous with said flat zones, one of said flat zones substantially coinciding with a first tangent line extending from a position on said central axis to said leading leaf end with the corresponding leaf in said fully retracted mode, the other of said flat zones substantially coinciding with a second tangent line extending from said central axis to said leaf end with said corresponding leaf in said fully extended mode.

17. The collimator of claim 16 in which said intermediate zone is generally curved in profile.

18. The collimator of claim 16 in which said intermediate zone is generally polygonal in profile.

19. The collimator of claim 16 in which said collimator is arranged in two of said arrays with the leading ends of each array facing the other in opposed relationship on opposite sides of said central axis.

20. In a radiation therapy system including a ray source for producing a radiation field, the improvement comprising a multileaf collimator having a plurality of elongated leaves, each leaf being movable in a longitudinal direction to define a treatment field out of said radiation field which is variable in size and form dependent on the position of said leaves, each leaf including a leaf end extending in a direction transverse to said longitudinal direction, said leaf end having a central portion being symmetric about a point offset from a longitudinal centerline of said respective leaf.

21. The improvement of claim 20 further comprising a pair of straight end portions disposed on either side of said central portion and being continuous therewith.

22. The improvement of claim 20 in which said ray source defines a central axis, and in which each said leaf is movable transversely beyond a central axis coincident with said central axis of said ray source from a retracted position to an extended position intersecting said central axis, one of said straight end portions coinciding with a tangent line extending from the edge of said ray source to said leaf end when said leaf is disposed at said retracted position, and the other straight end portion coinciding with a tangent line extending from the edge of said ray source to said leaf end when said leaf end is disposed at said extended position.

23. The improvement of claim 22 wherein said leaves are movable to define a plurality of treatment fields simultaneously.

24. The improvement of claim 20 wherein said central portion includes one of a curved and polygonal configuration.

25. The improvement of claim 24 wherein the curvature of said central portion comprises a simple arc.

26. The improvement of claim 25 wherein said simple arc comprises a radius or polygon having a center point offset from the longitudinal center of said leaf.

27. The improvement of claim 20 wherein said plurality of leaves is arranged in a side-by-side array and wherein the configuration of each leaf end is determined by the position of each respective leaf in said array.

28. A leaf for use in a multileaf collimator, said leaf comprising an elongated body and a leaf end, said leaf end comprising a first planar end portion and a second planar end portion and a central portion having one of a curved and polygonal configuration, said central portion disposed between said first and second planar portions such that said first planar end portion and said second planar end portion are not colinear.

29. The leaf of claim 28 wherein said leaf is movable in a longitudinal direction between a first and second position, wherein said first planar end portion coincides with a tangent extending from the edge of a radiation source spaced from the leaf to a reference plane when said leaf is disposed at said first position and wherein said second planar end portion coincides with a tangent extending from the edge of said radiation source to said reference plane when said leaf is disposed in said second position.

30. A radiation therapy system comprising an x-ray source for producing a therapeutic radiation field having a central axis, a multileaf collimator having a plurality of elongated leaves movable about a central axis parallel to said central axis of said x-ray source to define said radiation field, each leaf being independently movable from a fully retracted position disposed on a first side of said central axis to a fully extended position extending beyond said central axis, each said leaf including a leaf end extending in a direction generally parallel to said central axis and comprising:
- a central non-linear portion defined by a simple radius symmetric about a point offset distally from the longitudinal axis of the leaf;
- a first planar end portion disposed proximate said x-ray source and coinciding with a tangent extending from the edge of said x-ray source to said leaf end when said leaf end is disposed at said fully extended position; and
- a second planar end portion disposed distal from said x-ray source and coinciding with a tangent extending from the edge of said x-ray source to said leaf end when said leaf end is disposed at said fully retracted position.

* * * * *